United States Patent [19]

Löher et al.

[11] Patent Number: 4,776,875
[45] Date of Patent: Oct. 11, 1988

[54] FUNCTIONAL ACETIC ACID DERIVATIVES CONTAINING PHOSPHORUS AND HERBICIDAL, GROWTH-REGULATING AGENTS CONTAINING THEM

[75] Inventors: Heinz J. Löher, Frankfurt am Main; Klaus Bauer, Rodgau; Hermann Bieringer, Eppstein, all of Fed. Rep. of Germany

[73] Assignee: Hoechst Aktiengesellschaft, Frankfurt am Main, Fed. Rep. of Germany

[21] Appl. No.: 844,472

[22] Filed: Mar. 26, 1986

[30] Foreign Application Priority Data

Mar. 28, 1985 [DE] Fed. Rep. of Germany ....... 3511198

[51] Int. Cl.⁴ .......................... A01N 57/18; C07F 9/53

[52] U.S. Cl. ............................................ 71/86; 71/87; 540/542; 544/149; 544/157; 546/22; 548/413; 549/218; 558/45; 558/231; 558/386; 560/12; 560/24; 560/29; 560/32; 560/33; 560/35; 560/60; 560/61; 560/103; 560/105; 560/115; 560/129; 560/130; 560/132; 560/137; 560/144; 560/145; 560/148; 560/155; 560/157; 560/160; 560/162; 560/163; 560/165; 560/168; 560/172; 560/179; 560/185; 560/187; 560/188; 560/189; 560/222; 560/731; 564/13

[58] Field of Search .................. 549/218; 558/45, 231, 558/386; 560/12, 24, 29, 32, 33, 60, 61, 148, 157, 160, 162, 163, 165, 179, 185, 187, 188, 189; 71/86, 87

[56] References Cited

U.S. PATENT DOCUMENTS 4,594,098  6/1986  Bauer et al. ..................... 560/179

Primary Examiner—Richard L. Raymond
Attorney, Agent, or Firm—Curtis, Morris & Safford

[57] ABSTRACT

Compounds of the formula

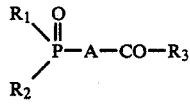

in which $R_1$ and $R_2$ denote alkyl, OH, $CF_3$ or cyanoethyl, A preferably denotes —COOH, $R_3$ denotes inter alia alkoxycarbonylalkoxy, fairly high-molecular ($>C_{12}$) alkoxy, alkylcarbonylalkoxy or nitrobenzyloxy, are valuable herbicides and growth regulators.

7 Claims, No Drawings

FUNCTIONAL ACETIC ACID DERIVATIVES CONTAINING PHOSPHORUS AND HERBICIDAL, GROWTH-REGULATING AGENTS CONTAINING THEM

The phosphonoglycine of the formula $(HO)_2P(O)CH(NH_2))COOH$ is described in Japanese Application 54.089,027 as a compound having herbicidal properties. Numerous derivatives of dimethylphosphinoylhydroxyacetic acid $(CH_3)_2P(O)CH(OH)COOH$ and related compounds are also disclosed in German Offenlegungsschrift 3,238,958.

It has now been found that numerous other functional derivatives, containing phosphorus, of acetic acid possess an excellent herbicidal and growth-regulating action.

The invention therefore relates to compounds of the general formula I

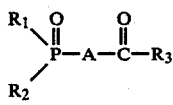

in which
$R_1$ and $R_2$ independently of one another denote $(C_1-C_4)$-alkyl, OH, $CF_3$ or cyanoethyl,
A denotes the groups —CO—, —CHOH, —CHOR$_6$, —CHOCONR$_7$R$_8$, —CHNHR$_9$ or —CHOCOR$_{10}$,
denotes —XCR$_{11}$R$_{12}$CXR$_{13}$, —X(C$_{13}$-C$_{18}$)-alkyl, —X-(C$_1$-C$_{17}$)-alkylcarbonyl-(C$_1$-C$_{17}$)-alkyl, nitrobenzyloxy, a radical of the formula

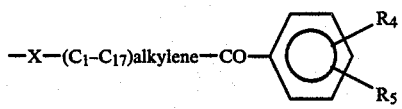

and, if A=—CHOCOR$_{10}$, also —OH or —SH; or $(C_1-C_{12})$-alkoxy, $(C_3-C_8)$-cycloalkoxy, $(C_3-C_6)$-alkenyloxy, $(C_3-C_6)$-alkinyloxy, phenoxy or benzyloxy, it being possible for the groups mentioned to be substituted in turn by OH, halogen, CF$_3$, $(C_1-C_4)$-alkyl or $(C_1-C_4)$-alkoxy; or $(C_1-C_6)$-alkylthio, $(C_3-C_8)$-cycloalkylthio, $(C_3-C_6)$-alkenylthio, $(C_3-C_6)$-alkinylthio, phenylthio or benzylthio, it being possible for the groups mentioned to be substituted in turn by halogen, CF$_3$, $(C_1-C_4)$-alkyl or $(C_1-C_4)$-alkoxy; or amino or hydroxylamino; or $(C_1-C_4)$-alkylamino, O-$(C_1-C_4)$-alkylhydroxylamino, di-$(C_1-C_4)$-alkylamino, anilino, phenyl-$(C_1-C_4)$-alkylamino, diphenyl-$(C_1-C_4)$-alkylamino, N-phenyl-N-$(C_1-C_4)$-alkylamino, N-phenyl-N-$(C_3-C_6)$-alkenylamino or N-phenyl-N-$(C_3-C_6)$-alkinylamino, it being possible for the groups mentioned to be substituted in turn by OH, halogen, $(C_1-C_4)$-alkyl or $(C_1-C_4)$-alkoxy; or hydrazino, β-$(C_1-C_4)$-alkylhydrazino, β,β-di-$(C_1-C_4)$-alkylhydrazino, piperidino, pyrrolidino, morpholino, 2,6-dimethylmorpholino or a radical of the formula

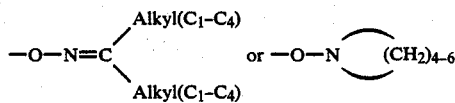

$R_4$ denotes H, OH, SH, halogen, $(C_1-C_4)$-alkyl, $(C_1-C_4)$-alkoxy, allyloxy, propargyloxy, phenoxy, benzyloxy, formyl, CF$_3$, NO$_2$, di-$(C_1-C_4)$-alkoxymethyl, di-$(C_1-C_4)$-alkylthiomethyl or $(C_1-C_4)$-alkoxycarbonyl,
$R_5$ denotes H, halogen, $(C_1-C_4)$-alkoxy or NO$_2$,
$R_6$ denotes $(C_1-C_{12})$-alkyl, benzyl, phenyl, halogenobenzyl, halogenophenyl, allyl, propargyl, CF$_3$ or tetrahydropyranyl,
$R_7$ and $R_8$ independently of one another denote H; or $(C_1-C_{12})$-alkyl, $(C_3-C_8)$-cycloalkyl, $(C_3-C_6)$-alkenyl, $(C_3-C_6)$-alkinyl, phenyl, benzyl, benzoyl, phenoxysulfonyl, $(C_1-C_{12})$-alkylsulfonyl, $(C_3-C_6)$-alkenylsulfonyl or phenylsulfonyl, it being possible for the groups mentioned to be substituted in turn by halogen, CF$_3$, CN, $(C_1-C_4)$-alkoxy or $(C_1-C_4)$-alkoxycarbonyl,
$R_9$ denotes hydrogen, $(C_1-C_6)$-alkyl, $(C_3-C_6)$-alkenyl, $(C_3-C_6)$-alkinyl, $(C_1-C_4)$-acyl, halogen-$(C_1-C_4)$-acyl or benzoyl,
$R_{10}$ denotes $(C_1-C_{18})$-alkyl, $(C_3-C_6)$-cycloalkyl, allyl, propargyl, phenyl, benzyl, monohalogenobenzyl, dihalogenobenzyl or aminomethyl,
$R_{11}$ and $R_{12}$ independently of one another denote H, $(C_1-C_4)$-alkyl, $(C_1-C_4)$-alkoxy, phenyl or benzyl,
$R_{13}$ denotes OH or SH; or $(C_1-C_{18})$-alkoxy, $(C_3-C_8)$-cycloalkoxy, $(C_3-C_{18})$-alkenyloxy, $(C_3-C_6)$-alkinyloxy, phenoxy or benzyloxy, it being possible for the groups mentioned to be substituted in turn by OH, halogen, CF$_3$, NO$_2$, $(C_1-C_4)$-alkyl, $(C_1-C_4)$-alkoxy or phenoxy; or $(C_1-C_4)$-alkoxycarbonyl-$(C_1-C_4)$-alkoxy, $(C_1-C_4)$-alkoxycarbonylbenzyloxy or benzyloxycarbonylbenzyloxy; or methylthio-$(C_1-C_4)$-alkyl, methylsulfinyl-$(C_1-C_4)$-alkyl or methylsulfonyl-$(C_1-C_4)$-alkyl; or $(C_1-C_{18})$-alkylthio, $(C_3-C_8)$-cycloalkylthio, $(C_3-C_{18})$-alkenylthio, $(C_3-C_6)$-alkinylthio, phenylthio or benzylthio, it being possible for the groups mentioned to be substituted in turn by halogen, CF$_3$, $(C_1-C_4)$-alkyl or $(C_1-C_4)$-alkoxy; or amino or hydroxylamino; or $(C_1-C_{12})$-alkylamino, O-$(C_1-C_4)$-alkylhydroxylamino, di-$(C_1-C_{10})$-alkylamino, anilino, phenyl-$(C_1-C_4)$-alkyl)amino, di[phenyl-$(C_1-C_4)$-alkyl]amino, N-phenyl-N-$(C_1-C_4)$-alkylamino, N-phenyl-N-$(C_3-C_6)$-alkenylamino or N-phenyl-N-$(C_3-C_6)$-alkinylamino, it being possible for the groups mentioned to be substituted in turn by OH, halogen, $(C_1-C_4)$-alkyl or $(C_1-C_4)$-alkoxy; or hydrazino,-$(C_1-C_4)$-alkylhydrazino, β,β-di-$(C_1-C_4)$-alkylhydrazino, piperidio, pyrrolindino, morpholino, 2,6-dimethylmorpholino or a radical of the formula

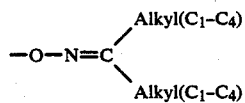

and X denotes O or S, and
to salts thereof with bases or acids.

In the above, "Hal" or "halogen" preferably denotes chlorine or bromine. If the aliphatic groups mentioned for $R_{13}$ are substituted, they are preferably monosubstituted by hydroxyl, $(C_1-C_4)$-alkoxy or halogen, especially chlorine. The aromatic groups can be monosubstituted to trisubstituted, preferably by halogen, in particular by chlorine, CF$_3$, $(C_1-C_2)$-alkyl or $(C_1-C_2)$-alkoxy.

If one of the radicals $R_1$, $R_2$ or $R_{13}$ denotes —OH or if $R_{13}$ denotes —SH, the compounds of the formula I are also capable of forming salts with inorganic and organic bases. Examples of suitable cations of bases are $Na^+$, $K^+$, $NH_4^+$, $Ca^{2+}$, $Mg^{2+}$, $Zn^{2+}$, $Cu^{2+}$, $Fe^{+2}$, $Ni^{2+}$, $(C_1-C_4)$-alkyl-$NH_3^+$, di-$(C_1-C_4)$-alkyl-$NH_2^+$, tri-$(C_1-C_4)$-alkyl-$NH^+$ or $(HOCH_2CH_2)_3NH^+$.

Compounds of the general formula I containing in the radicals A and $R_3$ one or more asymmetric carbon atoms or containing an asymmetric phosphorus atom, exist in enantiomeric or diastereomeric forms. In general, the corresponding compounds according to the invention are obtained in the form of racemates or mixtures of diastereomers. If desired, the customary techniques for the separation of the mixtures into the sterically, homogeneous constituents can be used. Preparation of the optical isomers in a pure state is also possible by using sterically homogeneous starting materials.

Compounds in which $R_1$ and $R_2$ denote $CH_3$ or $C_2H_5$; A denotes CHOH or $CHOCOR_{10}$ and $R_3$ denotes $OCH_2COR_{13}$, —$OCH(CH_3)COR_{13}$ or nitrobenzyloxy and $R_{13}$ has the meanings indicated are preferred.

Particularly preferred compounds are those in which $R_1$ and $R_2$ are $CH_3$, A is CHOH, $R_3$ is $OCH_2COR_{13}$, $OCH(CH_3)COR_{13}$ or nitrobenzyloxy and $R_{13}$ is $(C_1-C_{18})$-alkoxy, allyloxy, propinyloxy, $(C_1-C_4)$-halogenoalkoxy, $(C_1-C_4)$-alkoxycarbonyl-$(C_1-C_4)$-alkoxy, benzyloxy, $(C_1-C_4)$-alkoxycarbonylbenzyloxy, benzyloxycarbonylbenzyloxy, $(C_1-C_4)$-alkylthio, $(C_1-C_4)$-alkylamino, anilino or benzylamino.

Compounds of the formula I in which $R_3$ is —$XCR_{11}R_{12}CXR_{13}$ are obtained by reacting compounds of the general formula II

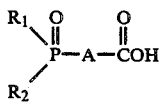

with halogeno(thio)carboxylic acids or esters of the formula III

      III or hydroxy(thio)carboxylic acid (esters) or mercapto(thio)carboxylic acid (esters) of the formula IV

      IV

Further compounds I in which $R_3$ is X-alkyl, X-alkylcarbonylalkyl, X-phenylcarbonylalkyl or nitrobenzyloxy are prepared in a manner analogous to the compounds of German Offenlegungsschrift 3,238,958.

The compounds of the formula I thus obtained can, if appropriate, be converted into other compounds of the formula I by alkylation, halogenation, benzylation, oxidation, acrylation, amination or hydrogenation. An alkoxy group which may be present in position $R_{13}$ can be saponified, or acids can be converted into their salts.

The reactions can be carried out with or without the addition of solvents at temperatures of 20°-100° C.; suitable solvents are, if appropriate, inert solvents, such as dioxane, tetrahydrofuran, acetonitrile, dimethoxyethane, methylene dichloride, toluene or dimethylformamide.

In some cases it is suitable to accelerate the reaction by adding bases. Suitable bases are alkali metal hydroxides or alcoholates, such as NaOH, KOH, $NaOCH_3$ or K tert.-butylate, or tertiary nitrogen bases, such as triethylamine or methyldiisopropylamine; and also fluorides, such as KF, CsF, or NaF.

The starting materials of the formulae II and V are obtained, for example, by the process indicated in German Offenlegungsschrift 3,238,958. The starting materials of the formulae III, IV and VI are known from the literature or can be prepared by processes known from the literature.

The compounds according to the invention possess an excellent and very broad herbicidal action against a broad spectrum of annual and perennial grass-like weeds and weeds on road verges, in industrial plants or in railroad installations. The invention also relates, therefore, to herbicidal agents containing the compounds of the formula I and to the use thereof for combating undesired plant growth.

The active compounds are suitable both for use in agriculture and for combating weeds. Use in annual or perennial agricultural crops is possible provided that the nature of the application and/or the age of the crop plant ensures that the crop plants or their sensitive green parts do not suffer damage. Examples of possible use of this type are plantations, tree nurseries, vineyards, etc.

Since using the new compounds in crops of useful plants before the emergence of the crop plants causes only slight damage or none at all, they can still be used against weeds before the emergence of the seed or before sowing or after the harvest.

However, the compounds according to the invention can also be employed even against plant growth of the useful plant (for example cotton or potatoes) which interferes in harvesting.

Depending on the dosage used, typical growth-regulating effects can also be achieved by means of the new compounds; thus, for example, it is possible to influence the growth of the plants, but also the content of desired plant constituents. The compounds are thereby suitable as growth regulators in crops of useful plants, such as, for example, cereals, maize, sugar cane, tobacco, rice and sorghum. On the other hand, it is also possible to regulate crops of plants, for instance cultivated lawns, or plant communities on the verges of paths and roads and also ornamental plants.

The effect of using the compounds according to the invention is to inhibit vegetative growth in a large number of monocotyledonous and dicotyledonous plants and, as a consequence thereof, to increase, inter alia, the carbohydrate content in the plants or in the fruit thereof. The consequence of this is in many cases an advantageous effect on the content of desired plant constituents, such as proteins or carbohydrates (starch or sugar).

For example, there is an increase in the sucrose content in the case of sugar cane and sugar beet, and of the levulose content in the case of fruit and grapes; in the case of other plants, such as potatoes, maize, millet (sorghum) and green fodder (clover and lucerne) there is an increase in the starch content. The advantages achieved thereby are manifest and require no explanation.

Application is effected about one week to 5 months before the harvest. After the expiration of this time the degree of ripeness, and hence also the carbohydrate content, caused by the active compounds has reached a maximum. In general it should be borne in mind that the rate of growth and vegetative period in the crops can vary within considerable limits. Sugar cane, for example, requires 1-3 years until it is ripe for harvesting, depending on its habitat and the climate. Similarly, the time of application must also be varied. In the case of sugar cane this can be, for example, 1 to 13 weeks before harvest.

The agents can be applied in the customary formulations as wettable powders, emulsifiable concentrates, atomizable solutions, dusting agents, dressing agents, dispersions, granules or microgranules.

Wettable powders are preparations which are uniformly dispersible in water and which, in addition to the active compound and apart, if appropriate, from a diluent or inert material, also contain wetting agents, for example polyoxethylated fatty alcohols, alkylsulfonates or alkylphenylsulfonates, and dispersing agents, for example sodium ligninsulfonate, sodium 2,2'-dinaphthylmethane-6,6'-disulfonate, sodium dibutylnaphthalenesulfonate or sodium oleoylmethyltauride. Preparation is effected in a customary manner, for example by grinding and mixing the components.

Emulsifiable concentrates can be prepared, for example, by dissolving the active compound in an inert organic solvent, for example butanol, cyclohexanone, dimethylformamide, xylene or fairly high-boiling aromatic compounds or hydrocarbons with the addition of one or more emulsifiers. In the case of liquid active compounds it is also possible to dispense, wholly or partly, with the solvent component. The following are examples of emulsifiers which can be used: calcium alkylarylsulfonates, such as Ca dodecylbenzenesulfonate, or nonionic emulsifiers, such as fatty acid polyglycol esters, alkylarylpolyglycol ethers, fatty alcohol polyglycol ethers, propylene oxide/ethylene oxide condensation products, fatty alcohol propylene oxide/ethylene oxide condensation products, alkyl polyglycol ethers, sorbitan fatty acid esters, polyoxethylenesorbitan fatty acid esters or polyoxethylenesorbitol esters.

Dusting agents can be obtained by grinding the active compound with finely divided solid materials, for example talc, natural clays, such as kaolin, bentonite or pyrophillite, or diatomaceous earth.

Granules can be prepared either by atomizing the active compound onto adsorptive, granulated inert material or by applying concentrations of active compound to the surface of carriers, such as sand, kaolinite or granulated inert material, by means of binders, for example polyvinyl alcohol, sodium polyacrylate or mineral oils. It is also possible to granulate suitable active compounds, if desired as a mixture with fertilizers, in the manner customary for the production of fertilizer granules.

In wettable powders the concentration of active compound is, for example, about 10 to 90% by weight; the remainder up to 100% by weight is composed of customary formulation ingredients. In the case of emulsifiable concentrates, the concentration of active compound can be about 10 to 80% by weight. Formulations in the form of dusts contain in most cases 5 to 20% by weight of active compound, while atomizable solutions contain about 2 to 20% by weight. In the case of granules, the content of active compound depends in part on whether the active compound is present as a liquid or solid and on the granulation auxiliaries, fillers and the like which are used.

In addition, the active compound formulations mentioned contain, if appropriate, the tackifiers, wetting agents, dispersing agents, emulsifiers, penetration agents, solvents, fillers or carriers which are customary in the particular case.

For application, the concentrates, present in a commercially customary form, are, if appropriate, diluted in a customary manner, for example with water in the case of wettable powders, emulsifiable concentrates and dispersions and, in part, also in the case of microgranules. Formulations in the form of dusts and granules and also atomizable solutions are usually not diluted further with other inert materials before application.

Mixtures or mixed formulations with other active compounds, such as, for example, insecticides, acaricides, herbicides, fertilizers, growth regulators or fungicides, are possible in a given case. Particularly in the case of mixtures with fungicides, synergistic increases in effectiveness can also be achieved in some cases.

The concentrations for application can vary within wide limits, depending on the purpose of use and the time of application. For use as herbicides, concentrations between 0.3 and 10, preferably 0.5 to 3, kg/hectare are suitable. When used as growth regulators, the concentrations for application are naturally lower and are approx. 0.1–2 kg/hectare, it being possible for the required concentration to vary considerably depending on the species of plant.

The invention is illustrated by the following examples.

EXAMPLE 1

Phenacyl 2-dimethylphosphinoyl-2-hydroxyacetate 6.38 g (0.1 mol) of potassium fluoride, 9.95 g (0.06 mol) of λ-bromoacetophenone and 7.6 g (0.05 mol) of 2-dimethylphosphinoyl-2-hydroxyacetic acid are dissolved in 250 ml of dimethylformamide, and the mixture is stirred for 4 hours at 65° C.; DMF is removed by distillation and the residue is stirred with $CH_2Cl_2$ to complete the reaction. Yield 8.5 g (63%), melting point 147° C.

The following compounds are obtained analogously:

TABLE 1

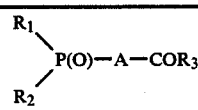

| Example No. | $R_1$ | $R_2$ | A | $R_3$ | M.p. [°C.] |
|---|---|---|---|---|---|
| 2 | $CH_3$ | $CH_3$ | CHOH | $-OCH_2C_6H_4NO_2(p)$ | 121 |
| 3 | $CH_3$ | $CH_3$ | CHOH | $-OCH_2C_6H_4NO_2(o)$ | |
| 4 | $CH_3$ | $CH_3$ | CHOH | $-OCH_2C_6H_4NO_2(m)$ | |
| 5 | $CH_3$ | $CH_3$ | CHOH | $-OCH_2COC_6H_4Br(p)$ | 163 |
| 6 | $CH_3$ | $CH_3$ | CHOH | $-OCH_2COC_6H_4Br(o)$ | |
| 7 | $CH_3$ | $CH_3$ | CHOH | $-OCH_2COC_6H_4Br(m)$ | |

TABLE 1-continued $$\begin{matrix} R_1 \\ \phantom{R_1}\diagdown \\ \phantom{R_1}P(O)-A-COR_3 \\ \phantom{R_1}\diagup \\ R_2 \end{matrix}$$

| Example No. | $R_1$ | $R_2$ | A | $R_3$ | M.p. [°C.] |
|---|---|---|---|---|---|
| 8 | $CH_3$ | $CH_3$ | CHOH | $-OCH_2COOH$ | Oil |
| 9 | $CH_3$ | $CH_3$ | CHOH | $-OCH_2-COOCH_3$ | 115 |
| 10 | $CH_3$ | $CH_3$ | CHOH | $-OCH_2-COOC_2H_5$ | 107 |
| 11 | $CH_3$ | $CH_3$ | CHOH | $-OCH_2-COOC_3H_7(n)$ | 82 |
| 12 | $CH_3$ | $CH_3$ | CHOH | $-OCH_2-COOC_6H_{13}(n)$ | 65–7 |
| 13 | $CH_3$ | $CH_3$ | CHOH | $-OCH_2-COOC_7H_{15}(n)$ | 72 |
| 14 | $CH_3$ | $CH_3$ | CHOH | $-OCH_2-COOC_{10}H_{21}(n)$ | 76–8 |
| 15 | $CH_3$ | $CH_3$ | CHOH | $-OCH_2-COOC_{12}H_{25}(n)$ | 88–90 |
| 16 | $CH_3$ | $CH_3$ | CHOH | $-OCH_2-COOC_{18}H_{37}(n)$ | 98–100 |
| 17 | $CH_3$ | $CH_3$ | CHOH | $-OCH_2-COOC_{18}H_{35}(n)$ (Oleyl) | Oil |
| 18 | $CH_3$ | $CH_3$ | CHOH | $-OCH_2-COOCH_2-CH(CH_3)-C_2H_5$ | Oil |
| 19 | $CH_3$ | $CH_3$ | CHOH | $-OCH_2-COOC_4H_9(tert.)$ | 118 |
| 20 | $CH_3$ | $CH_3$ | CHOH | $-OCH_2-COO-Cyclohexyl$ | Oil |
| 21 | $CH_3$ | $CH_3$ | CHOH | $-OCH_2-COOC_6H_{10}CH_3(o)$ | 130–4 |
| 22 | $CH_3$ | $CH_3$ | CHOH | $-OCH_2-COO-Cyclopropyl$ | Oil |
| 23 | $CH_3$ | $CH_3$ | CHOH | $-OCH_2-COO-CH_2C\equiv CH$ | Oil |
| 24 | $CH_3$ | $CH_3$ | CHOH | $-OCH_2-COOCH_2Br$ | Oil |
| 25 | $CH_3$ | $CH_3$ | CHOH | $-OCH_2COOCH_2CH_2Br$ | Oil |
| 26 | $CH_3$ | $CH_3$ | CHOH | $-OCH_2-COO-CH-CH_2$ with $O$, $O$ bridged by $C(CH_3)_2$ | Oil |
| 27 | $CH_3$ | $CH_3$ | CHOH | $-OCH_2-COOCH(CH_3)-COOC_2H_5$ | Oil |
| 28 | $CH_3$ | $CH_3$ | CHOH | $-OCH_2COO-CH(C_6H_5)-COOC_2H_5$ | Oil |
| 29 | $CH_3$ | $CH_3$ | CHOH | $-OCH_2COOCH(C_6H_5)COOCH_2C_6H_5$ | Oil |
| 30 | $CH_3$ | $CH_3$ | CHOH | $-OCH_2-COOCH_2C_6H_5$ | 95 |
| 31 | $CH_3$ | $CH_3$ | CHOH | $-OCH_2-COOCH_2C_6H_4CF_3(p)$ | |
| 32 | $CH_3$ | $CH_3$ | CHOH | $-OCH_2-COOCH_2C_6H_4CF_3(o)$ | |
| 33 | $CH_3$ | $CH_3$ | CHOH | $-OCH_2-COOCH_2C_6H_4CF_4(m)$ | |
| 34 | $CH_3$ | $CH_3$ | CHOH | $-OCH_2-COOCH_2C_6H_4NO_2(p)$ | 147 |
| 35 | $CH_3$ | $CH_3$ | CHOH | $-OCH_2-COOCH_2C_6H_4NO_2(o)$ | |
| 36 | $CH_3$ | $CH_3$ | CHOH | $-OCH_2-COOCH_2C_6H_4NO_2(m)$ | |
| 37 | $CH_3$ | $CH_3$ | CHOH | $-OCH_2-COOCH_2C_6H_3Cl_2(o, p)$ | Oil |
| 38 | $CH_3$ | $CH_3$ | CHOH | $-OCH_2-COOCH_2C_6H_4OC_6H_5(m)$ | 133 |
| 39 | $CH_3$ | $CH_3$ | CHOH | $-OCH_2COSC_2H_5$ | 83–6 |
| 40 | $CH_3$ | $CH_3$ | CHOH | $-OCH_2COSC_4H_9(n)$ | |
| 41 | $CH_3$ | $CH_3$ | CHOH | $-OCH_2COSC_{10}H_{21}(n)$ | |
| 42 | $CH_3$ | $CH_3$ | CHOH | $-OCH_2COSCH_2CH=CH_2$ | |
| 43 | $CH_3$ | $CH_3$ | CHOH | $-OCH_2COSCH_2C_6H_5$ | Oil |
| 44 | $CH_3$ | $CH_3$ | CHOH | $-OCH_2COSC_6H_5$ | Oil |
| 45 | $CH_3$ | $CH_3$ | CHOH | $-OCH_2CONH_2$ | |
| 46 | $CH_3$ | $CH_3$ | CHOH | $-OCH_2CONHC_2H_5$ | |
| 47 | $CH_3$ | $CH_3$ | CHOH | $-OCH_2CONHCH_2C_6H_5$ | Oil |
| 48 | $CH_3$ | $CH_3$ | CHOH | $-OCH_2CONHC_6H_5$ | Oil |
| 49 | $CH_3$ | $CH_3$ | CHOH | $-OCH_2CONHC_8H_{17}(n)$ | |
| 50 | $CH_3$ | $CH_3$ | $-CH-$ with $OCOC_6H_5$ | $-CH_3$ | 93–5 |
| 51 | $CH_3$ | $CH_3$ | $-CH-$ with $OCOC_{15}H_{31}(n)$ | $-CH_3$ | Oil |
| 52 | $CH_3$ | $CH_3$ | $-CH-$ with $OCOCH_2C_6H_3Cl_2(o, p)$ | $-CH_3$ | Oil |

TABLE 1-continued $$\begin{array}{c} R_1 \\ \diagdown \\ P(O)-A-COR_3 \\ \diagup \\ R_2 \end{array}$$

| Example No. | $R_1$ | $R_2$ | A | $R_3$ | M.p. [°C.] |
|---|---|---|---|---|---|
| 53 | $CH_3$ | $CH_3$ | —CH—<br>\|<br>$OCOCH_2NH_2$ | —$CH_3$ | |
| 54 | $CH_3$ | $CH_3$ | —CH—<br>\|<br>$OCOCH_2NH_2$ | —$CH_2C_6H_5$ | |
| 55 | $CH_3$ | $CH_3$ | CHOH | —$OCH_2$—$COS$—$C_6H_{13}(n)$ | Oil |
| 56 | $CH_3$ | $CH_3$ | CHOH | —$OCH_2$—$COS$—$C_{12}H_{25}(n)$ | 69–71 |
| 57 | $CH_3$ | $CH_3$ | CHOH | —$OCH_2$—$CON(C_2H_5)_2$ | 104–6 |
| 58 | $CH_3$ | $CH_3$ | CHOH | —$OCH_2$—$CON(C_8H_{17})_2(n)$ | Oil |
| 59 | $CH_3$ | $CH_3$ | CHOH | —$OCH_2$—$CONH$—$C_6H_3Cl_2(o, o)$ | 198 |
| 60 | $CH_3$ | $CH_3$ | CHOH | —$OC_2H_4COC_2H_5$ | |
| 61 | $CF_3$ | $CH_3$ | CHOH | —$OC_2H_4COC_2H_5$ | |
| 62 | $C_2H_5$ | $CH_3$ | CHOH | —$OC_2H_4COC_2H_5$ | |
| 63 | $CH_3$ | $CH_3$ | CHOH | —$OC_2H_4COC_4H_9(n)$ | |
| 64 | $C_2H_5$ | $CH_3$ | CHOH | —$OCH_2CONH_2$ | |
| 65 | $CH_3$ | $CH_3$ | CHOH | —$OCH_2CONH_2$ | |
| 66 | $CH_3$ | $CH_3$ | $CH-OCOC_6H_5$ | —$OCH_2CONHC_4H_9(n)$ | |
| 67 | $CH_3$ | $CH_3$ | $CH-OCOC_6H_5$ | —$OCH_2CONHC_4H_9(n)$ | |
| 68 | $CH_3$ | $CH_3$ | $CHOCOCH_2C_6H_5$ | —$OCH_2CONHOH$ | |
| 69 | $CH_3$ | $CH_3$ | $CHOCOCH_2C_6H_5$ | —$OCH_2CONHOH$ | |
| 70 | $CH_3$ | $CH_3$ | $CHOCOCH_2C_6H_5$ | —$OCH_2CONH$—$NH_2$ | |
| 71 | $CH_3$ | $CH_3$ | CHOH | —$OCH_2CONH$—$NH_2$ | |
| 72 | $CH_3$ | $CH_3$ | CHOH | —$OCH_2CO$—$N\underset{}{\bigcirc}O$ (morpholine) | |
| 73 | $CH_3$ | $CH_3$ | CHOH | —$OCH_2CO$—$N\underset{}{\bigcirc}O$ (morpholine) | |
| 74 | $CH_3$ | $CH_3$ | $CHNH_2$ | —$OCH_2HCOOC_2H_5$ | |
| 75 | $CH_3$ | $CH_3$ | $CHNHC_2H_5$ | —$OCH_2HCOOC_2H_5$ | |
| 76 | $CH_3$ | $CH_3$ | $CHNHC_2H_5$ | —$OCH_2COOCH_3$ | |
| 77 | $CH_3$ | $CH_3$ | $CHNHC_2H_5$ | —$OCH_2COOCH_2C_6H_5$ | |
| 78 | $CH_3$ | $CH_3$ | $CHOCH_3$ | —$OCH_2COOCH_3$ | |
| 79 | $C_2H_5$ | $CH_3$ | $CHOCH_3$ | —$OCH_2COOCH_3$ | |
| 80 | $C_2H_5$ | $CH_3$ | $CHOCH_3$ | —$OCH_2COOCH_3$ | |
| 81 | $C_2H_5$ | $CH_3$ | $CHOC_2H_5$ | —$OCH_2COOCH_3$ | |
| 82 | $C_2H_5$ | $CH_3$ | $CHOC_2H_5$ | —$OCH_2COOCH_3$ | |
| 83 | $C_2H_5$ | $CH_3$ | $CHOCH_2C_6H_5$ | —$OCH_2COOCH_3$ | |
| 84 | $CF_3$ | $CH_3$ | $CHOCH_2C_6H_5$ | —$OCH_2COOCH_3$ | |
| 85 | $CH_3$ | $CH_3$ | $CHOC_6H_4Cl(o)$ | —$OCH_2COOCH_3$ | |
| 86 | $CH_3$ | $CH_3$ | $CHOC_6H_4Cl(o)$ | —$OCH_2COOCH_3$ | |
| 87 | $CH_3$ | $CH_3$ | $CHOCON(CH_3)_2$ | —$OCH(CH_3)COOCH_3$ | |
| 88 | $C_2H_5$ | $CH_3$ | $CHOCON(CH_3)_2$ | —$OCH(CH_3)COOCH_3$ | |
| 89 | $C_4H_9(n)$ | $CH_3$ | $CHOCON(CH_3)_2$ | —$OCH(CH_3)COOCH_3$ | |
| 90 | $CF_3$ | $CH_3$ | $CHOCON(CH_3)_2$ | —$OCH(CH_3)COOCH_3$ | |
| 91 | OH | $CH_3$ | $CHOCON(CH_3)_2$ | —$OCH(CH_3)COOCH_3$ | |
| 92 | $CH_3$ | $CH_3$ | $CHOCONHC_6H_5$ | —$OCH(CH_3)COOC_2H_5$ | |
| 93 | $C_2H_5$ | $CH_3$ | $CHOCONHC_6H_5$ | —$OCH(CH_3)COOC_2H_5$ | |
| 94 | $C_4H_9(n)$ | $CH_3$ | $CHOCONHC_6H_5$ | —$OCH(CH_3)COOC_2H_5$ | |
| 95 | $CH_3$ | $CH_3$ | $CHOCOC_6H_5$ | —$OC(CH_3)_2COOCH_3$ | |
| 96 | $CF_3$ | $CH_3$ | $CHOCOC_6H_5$ | —$OCH(CH_3)COOC_2H_5$ | |
| 97 | OH | $CH_3$ | $CHOCOC_6H_5$ | —$OCH(CH_3)COOC_2H_5$ | |
| 98 | $C_4H_9(n)$ | $C_4H_9(n)$ | $CHOCOC_6H_5$ | —$OCH(CH_3)COOC_2H_5$ | |
| 99 | $CH_3$ | $CH_3$ | $CHOCOCH_2CH=CH_2$ | —$OCH_2$—$COOC_2H_5$ | |
| 100 | $CF_3$ | $CH_3$ | $CHOCOCH_2CH=CH_2$ | $SCH_2$—$COOCH_3$ | |
| 101 | $C_4H_9(n)$ | $C_4H_9(n)$ | $CHOCOCH_2CH=CH_2$ | $SCH_2$—$COOCH_3$ | |
| 102 | $C_2H_5$ | $CH_3$ | $CHOCOCH_2CH=CH_2$ | $SCH_2$—$COOCH_3$ | |
| 103 | $CH_2$—$CH_2$—CN | $CH_3$ | $CHOCON(CH_3)_2$ | —$OCH(CH_3)COOCH_3$ | |
| 104 | $CH_2$—$CH_2$—CN | $CH_3$ | $CHOCOC_6H_5$ | —$OCH(CH_3)COOC_2H_5$ | |
| 105 | $CH_2$—$CH_2$—CN | $CH_3$ | $CHOCOCH_2$—$CH=CH_2$ | —$OCH(CH_3)COOC_4H_9(n)$ | |
| 106 | $CH_2$—$CH_2$—CN | $CH_3$ | $CHOCONHC_6H_5$ | —$OCH(CH_3)COOC_2H_5$ | |
| 107 | $CH_2$—$CH_2$—CN | $CH_3$ | $CHOCONHC_6H_5$ | —$OCH(CH_3)COOC_6H_4NO_2(m)$ | |
| 108 | $C_2H_5$ | $CH_3$ | $CHOCOC_6H_5$ | —$OCH(CH_3)COOC_6H_4NO_2(m)$ | |
| 109 | $CF_3$ | $CH_3$ | $CHOCOC_6H_5$ | —$OCH(CH_3)COOC_6H_4NO_2(m)$ | |

TABLE 1-continued $$\begin{array}{c}R_1\\ \diagdown\\ P(O)-A-COR_3\\ \diagup\\ R_2\end{array}$$

| Example No. | $R_1$ | $R_2$ | A | $R_3$ | M.p. [°C.] |
|---|---|---|---|---|---|
| 110 | $C_4H_9(n)$ | $CH_3$ | $CHOCOC_6H_5$ | $-OCH(CH_3)COOC_6H_4NO_2(m)$ | |
| 111 | $CH_3$ | $CH_3$ | $CHOCON(CH_3)_2$ | $-OCH(CH_3)COOC_6H_4NO_2(m)$ | |
| 112 | $C_3H_7(i)$ | $CH_3$ | $CHOCON(CH_3)_2$ | $-OCH(CH_3)COOC_6H_4NO_2(m)$ | |
| 113 | $C_3H_7(i)$ | $C_3H_7(i)$ | $CHOCON(CH_3)_2$ | $-OCH(CH_3)COOC_6H_4NO_2(m)$ | |
| 114 | $CH_3$ | $CH_3$ | $CHOCOC_6H_5$ | OH | |
| 115 | $CH_3$ | $CH_3$ | $CHOCOC_6H_5$ | SH | |
| 116 | $CH_3$ | $CH_3$ | $CHOCOC_6H_5$ | $OCH_3$ | |
| 117 | $CH_3$ | $CH_3$ | $CHOCOC_6H_5$ | $OC_2H_5$ | |
| 118 | $CH_3$ | $CH_3$ | $CHOCOC_6H_5$ | $OCH_2-C_6H_5$ | |
| 119 | $CH_3$ | $CH_3$ | $CHOCOC_6H_5$ | $SCH_2-C_6H_5$ | |
| 120 | $CH_3$ | $CH_3$ | $CHOCOC_6H_5$ | $OC_6H_4OC_6H_5(p)$ | |
| 121 | $CH_3$ | $CH_3$ | $CHOCOC_6H_5$ | $OC_6H_4OC_6H_5(m)$ | |
| 122 | $CH_3$ | $CH_3$ | $CHOCOC_6H_5$ | $N(C_2H_5)_2$ | |
| 123 | $CH_3$ | $CH_3$ | $CHOCOC_6H_5$ | $NH_2$ | |
| 124 | $CH_3$ | $CH_3$ | $CHOCOC_6H_5$ | $NHC_2H_5$ | |
| 125 | $CH_3$ | $CH_3$ | CHOH | $-OCH_2COOCH_2COOC_2H_5$ | |
| 126 | $CH_3$ | $CH_3$ | CHOH | $-OCH_2COOC_2H_4-COOCH_3$ | |
| 127 | $CH_3$ | $CH_3$ | CHOH | $-OCH_2-COOCH_2C_6H_4-COOCH_2C_6H_5(p)$ | |
| 128 | $CH_3$ | $CH_3$ | CHOH | $-OCH_2COOCH_2C_6H_4COOC_2H_5(p)$ | |
| 129 | $CH_3$ | $CH_3$ | CHOH | $-O-CH_2COOCH_2-COOC_4H_9(n)$ | |

(B) Formulation Examples (a) A dusting agent is obtained by mixing 10 parts by weight of active compound and 90 parts by weight of talc or an inert substance and comminuting the mixture in a hammer mill.

(b) A wettable powder which is readily dispersible in water is obtained by mixing 25 parts by weight of active compound, 64 parts by weight of kaolin-containing quartz as an inert substance, 10 parts by weight of potassium ligninsulfonate and 1 part by weight of sodium oleoylmethyltauride as a wetting and dispersing agent, and grinding the mixture in a pinned disk mill.

(c) A dispersion concentrate which is readily dispersible in water is obtained by mixing 20 parts by weight of active compound with 6 parts by weight of an alkylphenol polyglycol ether (Triton X 207), 3 parts by weight of isotridecanol polyglycol ether (8 EO) and 71 parts by weight of paraffinic mineral oil (boiling range, for example, approx. 255° to over 377° C.), and grinding the mixture in a ball mill to a fineness of less than 5 microns.

(d) An emulsifiable concentrate is obtained from 15 parts by weight of active compound, 75 parts by weight of cyclohexanone as solvent and 10 parts by weight of oxethylated nonylphenol (10 EO) as emulsifier.

(c) Biological Examples

EXAMPLE 1

Seeds or pieces of rhizome of grass-like weeds and weeds were sown in sandy loam soil in plastic pots ($\phi$ 9 cm) and were cultivated in a greenhouse under good growth conditions for 3–5 weeks. The compounds according to the invention, formulated as wettable powders or aqueous solutions, were then sprayed onto the parts of the plants above ground in the form of aqueous suspensions or atomizable solutions, respectively. The amount of water used corresponded to 600–800 liters/hectare.

After approx. 3 weeks waiting time in a greenhouse under optimal conditions for growth, the herbicidal action was assessed visually.

The results of the tests with the new compounds according to the invention are assembled in Table 2. The following code was used in these tests:

0=no action
1=0–20% action
2=20–40% action
3=40–60% action
4=60–80% action
5=80–100% action The figures shown in Table 2 afford clear proof of the very good herbicidal effectiveness of the new compounds against a broad spectrum of economically important weeds.

Abbreviations used in Table 2

SIA=*Sinapis arvensis*
CRS=*Crysanthemum segctum*
ECG=*Echinochloa crus galli*
LOM=*Lolium multiflorum*
a.i.=active ingredient

TABLE 2

Herbicidal effect of the compounds, according to the invention, used in the post-emergence technique

| Example No. | Dosage kg of a.i./hectare | Herbicidal effect | | | |
|---|---|---|---|---|---|
| | | SIA | CRS | ECG | LOM |
| 2 | 2.5 | 5 | 5 | 4 | 5 |
| 1 | 2.5 | 5 | 5 | 4 | 5 |
| 5 | 2.5 | 5 | 4 | 5 | 5 |
| 8 | 2.5 | 5 | 5 | 5 | 5 |
| 9 | 2.5 | 5 | 4 | 5 | 5 |
| 10 | 2.5 | 5 | 4 | 4 | 5 |
| 11 | 2.5 | 5 | 5 | 5 | 5 |
| 12 | 2.5 | 5 | 5 | 5 | 5 |
| 14 | 2.5 | 5 | 5 | 5 | 5 |
| 15 | 2.5 | 5 | 3 | 3 | 4 |
| 16 | 2.5 | 5 | 4 | 4 | 5 |
| 17 | 2.5 | 5 | 3 | 2 | 4 |
| 18 | 2.5 | 5 | 5 | 5 | 5 |
| 19 | 2.5 | 5 | 5 | 4 | 5 |
| 20 | 2.5 | 4 | 1 | 1 | 1 |

TABLE 2-continued

Herbicidal effect of the compounds, according to the invention, used in the post-emergence technique

| Example No. | Dosage kg of a.i./hectare | Herbicidal effect | | | |
|---|---|---|---|---|---|
| | | SIA | CRS | ECG | LOM |
| 21 | 2.5 | 5 | 4 | 4 | 5 |
| 22 | 2.5 | 3 | 1 | 1 | 1 |
| 23 | 2.5 | 5 | 5 | 4 | 5 |
| 24 | 2.5 | 5 | 4 | 4 | 5 |
| 25 | 2.5 | 5 | 4 | 5 | 5 |
| 26 | 2.5 | 4 | 1 | 1 | 1 |
| 27 | 2.5 | 5 | 5 | 5 | 5 |
| 28 | 2.5 | 5 | 4 | 4 | 5 |
| 29 | 2.5 | 5 | 4 | 3 | 3 |
| 30 | 2.5 | 5 | 5 | 5 | 5 |
| 31 | 2.5 | 4 | 4 | 4 | 5 |
| 34 | 2.5 | 5 | 4 | 2 | 3 |
| 37 | 2.5 | 5 | 1 | 1 | 1 |
| 38 | 2.5 | 5 | 3 | 2 | 2 |
| 39 | 2.5 | 5 | 4 | 5 | 5 |
| 43 | 2.5 | 4 | 4 | 4 | 4 |
| 47 | 2.5 | 5 | 5 | 5 | 5 |
| 48 | 2.5 | 5 | 4 | 4 | 5 |
| 55 | 2.5 | 5 | 5 | 5 | 5 |
| 56 | 2.5 | 2 | 1 | 1 | 1 |
| 57 | 2.5 | 4 | 5 | 5 | 5 |
| 58 | 2.5 | 5 | 4 | 4 | 3 |
| 59 | 2.5 | 5 | 5 | 5 | 5 |

We claim:

1. A compound of formula I

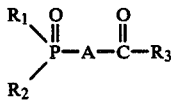

in which
$R_1$ and $R_2$ may be the same or different and each is $(C_1-C_4)$-alkyl, $CF_3$ or cyanoethyl;
A is $-CHOH-$, $-CHOR_6$, $-CHOCONR_7R_8$ or $-CHOCOR_{10}$;
$R_3$ is $-XCR_{11}R_{12}CXR_{13}$, $-X(C_1-C_{17})$-alkylcarbonyl-$(C_1-C_{17})$-alkyl, nitrobenzyloxy or a radical of the formula

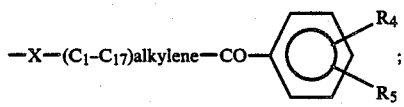

$R_4$ is H, OH, SH, halogen, $(C_1-C_4)$-alkyl, $(C_1-C_4)$-alkoxy, allyloxy, propargyloxy, phenoxy, benzyloxy, formyl, $CF_3$, $NO_2$, di-$(C_1-C_4)$-alkoxymethyl, di-$(C_1-C_4)$-alkylthiomethyl or $(C_1-C_4)$-alkoxycarbonyl;
$R_5$ is H, halogen, $(C_1-C_4)$-alkoxy or $NO_2$;
$R_6$ denotes $(C_1-C_{12})$-alkyl, benzyl, phenyl, halogenobenzyl, halogenophenyl, allyl, propargyl, $CF_3$ or tetrahydropyranyl,
$R_7$ and $R_8$ may be the same or different and each is H, $(C_1-C_{12})$-alkyl, $(C_3-C_8)$-cycloalkyl, $(C_3-C_6)$-alkenyl, $(C_3-C_6)$-alkinyl, phenyl, benzyl, benzoyl, phenoxysulfonyl, $(C_1-C_{12})$-alkylsulfonyl, $(C_3-C_6)$-alkenylsulfonyl or phenylsulfonyl, it being possible for the groups mentioned to be substituted in turn by halogen, $CF_3$, CN, $(C_1-C_4)$-alkoxy or $(C_1-C_4)$-alkoxycarbonyl;
$R_{10}$ is $(C_1-C_{18})$-alkyl, $(C_3-C_6)$-cycloalkyl, allyl, propargyl, phenyl, benzyl, monohalogenobenzyl, dihalogenobenzyl or aminomethyl;
$R_{11}$ and $R_{12}$ may be the same or different and each is H, $(C_1-C_4)$-alkyl, $(C_1-C_4)$-alkoxy, phenyl or benzyl;
$R_{13}$ is: OH or SH; $(C_1-C_{18})$-alkoxy, $(C_3-C_8)$-cycloalkoxy, $(C_3-C_{18})$-alkenyloxy, $(C_3-C_6)$-alkinyloxy, phenoxy or benzyloxy, it being possible for the groups mentioned to be substituted in turn by OH, halogen, $CF_3$, $NO_2$, $(C_1-C_4)$-alkyl, $(C_1-C_4)$-alkoxy or phenoxy; $(C_1-C_4)$-alkoxycarbonyl-$(C_1-C_4)$-alkoxy, $(C_1-C_4)$-alkoxycarbonylbenzyloxy or benzyloxycarbonylbenzyloxy; methylthio-$(C_1-C_4)$-alkyl, methylsulfinyl-$(C_1-C_4)$-alkyl or methylsulfonyl-$(C_1-C_4)$-alkyl; $(C_1-C_{18})$-alkylthio, $(C_3-C_8)$-cycloalkylthio, $(C_3-C_{18})$-alkenylthio, $(C_3-C_6)$-alkinylthio, phenylthio or benzylthio, it being possible for the groups mentioned to be substituted in turn by halogen, $CF_3$, $(C_1-C_4)$-alkyl or $(C_1-C_4)$-alkoxy; amino or hydroxylamino; $(C_1-C_4)$-alkylamino, O-$(C_1-C_4)$-alkylhydroxylamino, di-$(C_1-C_{10})$-alkylamino, anilino, phenyl-$(C_1-C_4)$-alkyl)amino, di[phenyl-$(C_1-C_4)$-alkyl]amino, N-phenyl-N-$(C_1-C_4)$-alkylamino, N-phenyl-N-$(C_3-C_6)$-alkenylamino or N-phenyl-N-$(C_3-C_6)$-alkinylamino, it being possible for the groups mentioned to be substituted in turn by OH, halogen, $(C_1-C_4)$-alkyl or $(C_1-C_4)$-alkoxy; or hydrazino, $\beta$-$(C_1-C_4)$-alkylhydrazino, $\beta,\beta$-di-$(C_1-C_4)$-alkylhydrazino, piperidino, pyrrolidino, morpholino, 2,6-dimethylmorpholino or a radical of the formula

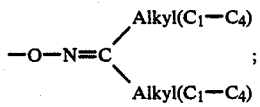

and X is O or S;
and salts thereof with bases or acids.

2. A compound as claimed in claim 1, in which $R_1$ and $R_2$ are $CH_3$ or $C_2H_5$, A is CHOH, $R_3$ is $-OCH_2COR_{13}$ or nitrobenzyloxy and $R_{13}$ has the meanings indicated in claim 1.

3. A compound as claimed in claim 2, in which $R_1$ and $R_2$ are methyl, A is CHOH and $R_{13}$ is $(C_1-C_{18})$-alkoxy, allyloxy, propinyloxy, $(C_1-C_4)$-halogenoalkoxy, $(C_1-C_4)$-alkoxycarbonyl-$(C_1-C_4)$-alkoxy, benzyloxy, $(C_1-C_4)$-alkoxycarbonylbenzyloxy, benzyloxycarbonylbenzyloxy, $(C_1-C_4)$-alkylthio, $(C_1-C_4)$-alkylamino, anilino or benzylamino.

4. The compound of claim 3 in which $R_1$ and $R_2$ are methyl, A is CHOH and $R_3$ is $-OCH_2-COOCH_3$.

5. A herbicidal and growth-regulating agent which comprises an effective amount of a compound as claimed in claim 1 and an inert carrier.

6. A process for combating undesired plant growth, which comprises applying an effective amount of a compound as claimed in claim 1 to the plants or to the areas to be treated.

7. A process for regulating the growth of useful plants, which comprises applying an effective amount of a compound as claimed in claim 1 to the plants.

* * * * *